(12) United States Patent
Akhlaghpour et al.

(10) Patent No.: US 11,786,379 B2
(45) Date of Patent: Oct. 17, 2023

(54) SYSTEM AND METHOD FOR IMPLANT VERIFICATION

(71) Applicant: THINK SURGICAL, INC., Fremont, CA (US)

(72) Inventors: Hosna Akhlaghpour, Fremont, CA (US); Nathan Netravali, Fremont, CA (US); In K. Mun, Fremont, CA (US)

(73) Assignee: Think Surgical, Inc., Fremont, CA (US)

( * ) Notice: Subject to any disclaimer, the term of this patent is extended or adjusted under 35 U.S.C. 154(b) by 245 days.

(21) Appl. No.: 16/637,784

(22) PCT Filed: Aug. 9, 2018

(86) PCT No.: PCT/US2018/046012
§ 371 (c)(1),
(2) Date: Feb. 10, 2020

(87) PCT Pub. No.: WO2019/032828
PCT Pub. Date: Feb. 14, 2019

(65) Prior Publication Data
US 2020/0197191 A1    Jun. 25, 2020

Related U.S. Application Data

(60) Provisional application No. 62/544,103, filed on Aug. 11, 2017.

(51) Int. Cl.
*A61B 34/20* (2016.01)
*A61F 2/46* (2006.01)
(Continued)

(52) U.S. Cl.
CPC ............. *A61F 2/468* (2013.01); *A61B 17/15* (2013.01); *A61B 17/17* (2013.01); *A61B 34/20* (2016.02);
(Continued)

(58) Field of Classification Search
CPC ..................................... A61B 34/20–2034/258
See application file for complete search history.

(56) References Cited

U.S. PATENT DOCUMENTS 5,682,886 A * 11/1997 Delp ...................... A61B 90/36
600/407
7,166,114 B2 * 1/2007 Moctezuma De La Barrera ........
G16H 40/40
606/1

(Continued)

FOREIGN PATENT DOCUMENTS

KR    1020150125069 A    11/2015
WO    2016-094298 A1     6/2016

OTHER PUBLICATIONS

Int'l. Search Report for PCT/US2018/046012, dated Mar. 5, 2019.

*Primary Examiner* — Zade Coley
(74) *Attorney, Agent, or Firm* — MaxGoLaw PLLC

(57) ABSTRACT

A system and method for intra-operatively measuring or verifying the placement of an implant within a bone in joint arthroplasty procedures are described herein. Pre-operative bone data of the patient is collected. A user plans the position of one or more implants relative to the pre-operative bone data. Intra-operatively, the patients bone is registered to the pre-operative bone data and to a computer-assist device. The bone is prepared and a physical implant is installed with the bone. A plurality of points are digitized on at least one of the physical implant or an apparatus associated with the physical implant. The computer-assist device calculates any errors between the planned position and orientation (POSE) of the implant relative to the actual POSE of the physical implant using the digitized points. The system may further notify a user of any errors and provide instructions to minimize the errors.

29 Claims, 10 Drawing Sheets

(51) Int. Cl.
 *A61B 34/37* (2016.01)
 *A61B 17/15* (2006.01)
 *A61B 17/17* (2006.01)
 A61B 34/10 (2016.01)
 A61B 34/00 (2016.01)
 A61F 2/36 (2006.01)

(52) U.S. Cl.
 CPC ............ *A61B 34/37* (2016.02); *A61F 2/4657* (2013.01); *A61F 2/4684* (2013.01); *A61B 2034/102* (2016.02); *A61B 2034/105* (2016.02); *A61B 2034/252* (2016.02); *A61B 2034/743* (2016.02); *A61B 2034/744* (2016.02); *A61F 2/36* (2013.01); *A61F 2002/4633* (2013.01)

(56) References Cited

U.S. PATENT DOCUMENTS

| | | | |
|---|---|---|---|
| 7,542,791 B2 * | 6/2009 | Mire | G16H 50/50 600/407 |
| 2008/0119724 A1 | 5/2008 | Williamson | |
| 2012/0271613 A1 * | 10/2012 | Ashby | G16H 30/20 703/11 |
| 2015/0182236 A1 * | 7/2015 | Dardenne | A61B 17/1703 606/281 |
| 2015/0305828 A1 | 10/2015 | Park et al. | |
| 2016/0228192 A1 | 8/2016 | Jansen et al. | |

\* cited by examiner

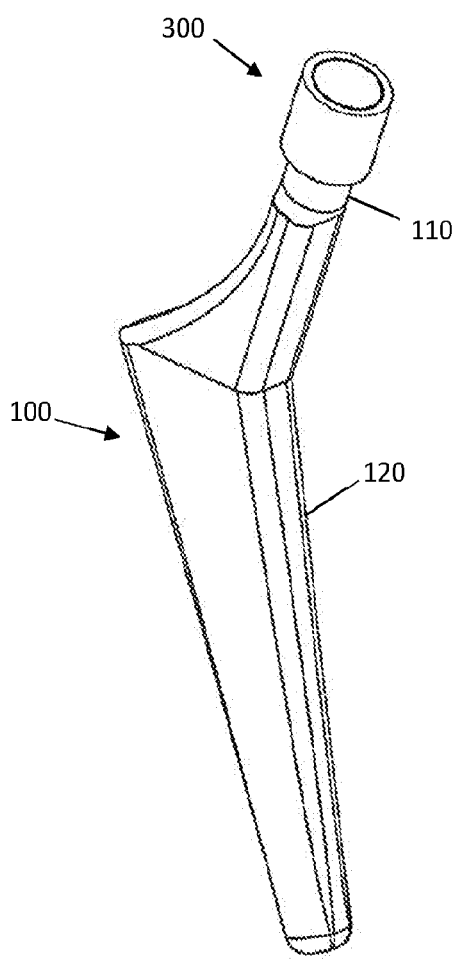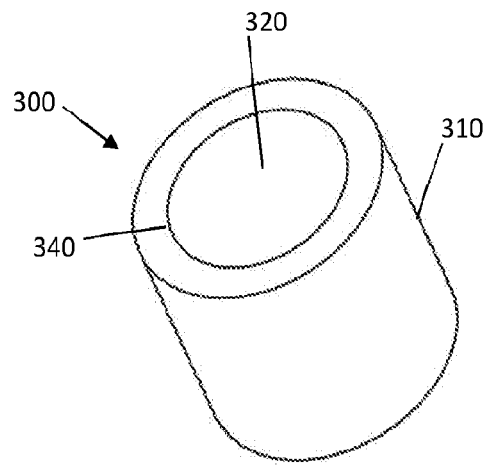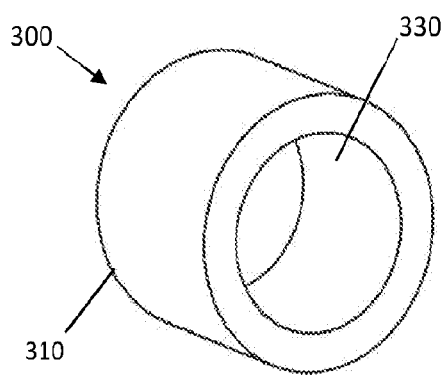
FIG. 2A
FIG. 2B
FIG. 2C (Detail A)

SYSTEM AND METHOD FOR IMPLANT VERIFICATION

RELATED APPLICATIONS

This application claims priority benefit of U.S. Provisional Application Ser. No. 62/544,103 filed 11 Aug. 2017; the contents of which are hereby incorporated by reference.

FIELD OF THE INVENTION

The present invention generally relates to the field of computer-assisted orthopedic surgery, and more particularly to a new and useful system and method for measuring or verifying the placement of an implant within a bone in joint arthroplasty procedures.

BACKGROUND

Throughout a lifetime, bones and joints become damaged and worn through normal use, disease, and traumatic events. Arthritis is a leading cause of joint damage, which can cause cartilage degradation, pain, swelling, stiffness, and bone loss overtime. Arthritis can also cause the muscles articulating the joints to lose strength and become very painful.

If the pain associated with the dysfunctional joint is not alleviated by less-invasive therapies, a joint arthroplasty procedure is considered as a treatment. Joint arthroplasty is an orthopedic procedure in which an arthritic or dysfunctional joint surface is replaced with an orthopedic prosthesis, or implant.

The accurate placement and alignment of an implant is a large factor in determining the success of joint arthroplasty. A slight misalignment may result in poor wear characteristics, reduced functionality, poor clinical outcomes, and decreased longevity.

In order to achieve accurate implant placement and alignment, a surgeon may use a computer-assist device (e.g., a surgical robot) to pre-operatively plan the position and orientation (POSE) of the implant relative to the bone prior to modifying the bone. One problem associated with the use of a computer-assisted device in joint arthroplasty is the difficulty in measuring and/or verifying the placement of the physical implant within the bone and compare that placement with the pre-operatively planned placement during the procedure, intra-operatively. Surgeons may currently use an imaging system (e.g., x-rays, computed tomography (CT), magnetic resonance imaging (MRI)) to identify the placement of the implant after the procedure, post-operatively, and compare the images to the pre-operative plan. However, these techniques do not allow the surgeon to measure, adjust, and minimize implant placement errors intra-operatively without exposing the patient to x-rays or other potentially harmful imaging techniques. In addition, comparing and identifying errors between intra-operative 2-D images of the implant placement and pre-operative 3-D models of the planned implant placement is rather difficult to perform accurately, in multiple degrees-of-freedom, and in a timely practical manner during surgery.

Thus, there is a need in the art for a system and method to more efficiently measure or verify the placement of the implant intraoperatively relative to the pre-operatively planned implant placement. There is a further need to utilize the measurements to optimize implant placement intra-operatively.

SUMMARY

A method for measuring or verifying the placement of an implant within a bone in joint arthroplasty procedures is provided herein. The position and orientation (POSE) of an implant model is planned relative to pre-operative bone data of a bone as part of a surgical plan for a subject patient. The bone is registered to the pre-operative bone data and a computer-assist device. A plurality of points are digitized on an apparatus associated with the physical implant after the physical implant is installed with the bone. Errors are determined between at least a portion of an actual POSE of the physical implant relative to the planned POSE using the plurality of digitized points.

A surgical system for performing a method for measuring or verifying the placement of an implant within a bone in joint arthroplasty procedures is also provided herein. The system includes a surgical robot and a workstation having a computer, user-peripherals, and a monitor for displaying a graphical user interface (GUI). The computer further includes a processor, non-transient storage memory, and other hardware, software, data, and utilities to execute the method for measuring or verifying the placement of an implant within a bone. The user peripherals allow a user to interact with the GUI and include user input mechanisms comprising at least of a keyboard, mouse, or a touchscreen monitor.

BRIEF DESCRIPTION OF THE DRAWINGS

Examples illustrative of embodiments are described below with reference to figures attached hereto. In the figures, identical structures, elements or parts that appear in more than one figure are generally labeled with a same numeral in all the figures in which they appear. Dimensions of components and features shown in the figures are generally chosen for convenience and clarity of presentation and are not necessarily shown to scale. The figures are listed below.

FIGS. 2A-2C depict an implant with an apparatus for the purpose of total hip replacement; where FIG. 2A depicts an apparatus coupled to an implant neck; FIG. 2B depicts a front view of the apparatus; and FIG. 2C depicts a rear view thereof;

FIG. 3A depicts a front view of the multi-size apparatus, and the FIG. 3B depicts a rear view thereof;

DETAILED DESCRIPTION OF THE INVENTION

Figure 1:
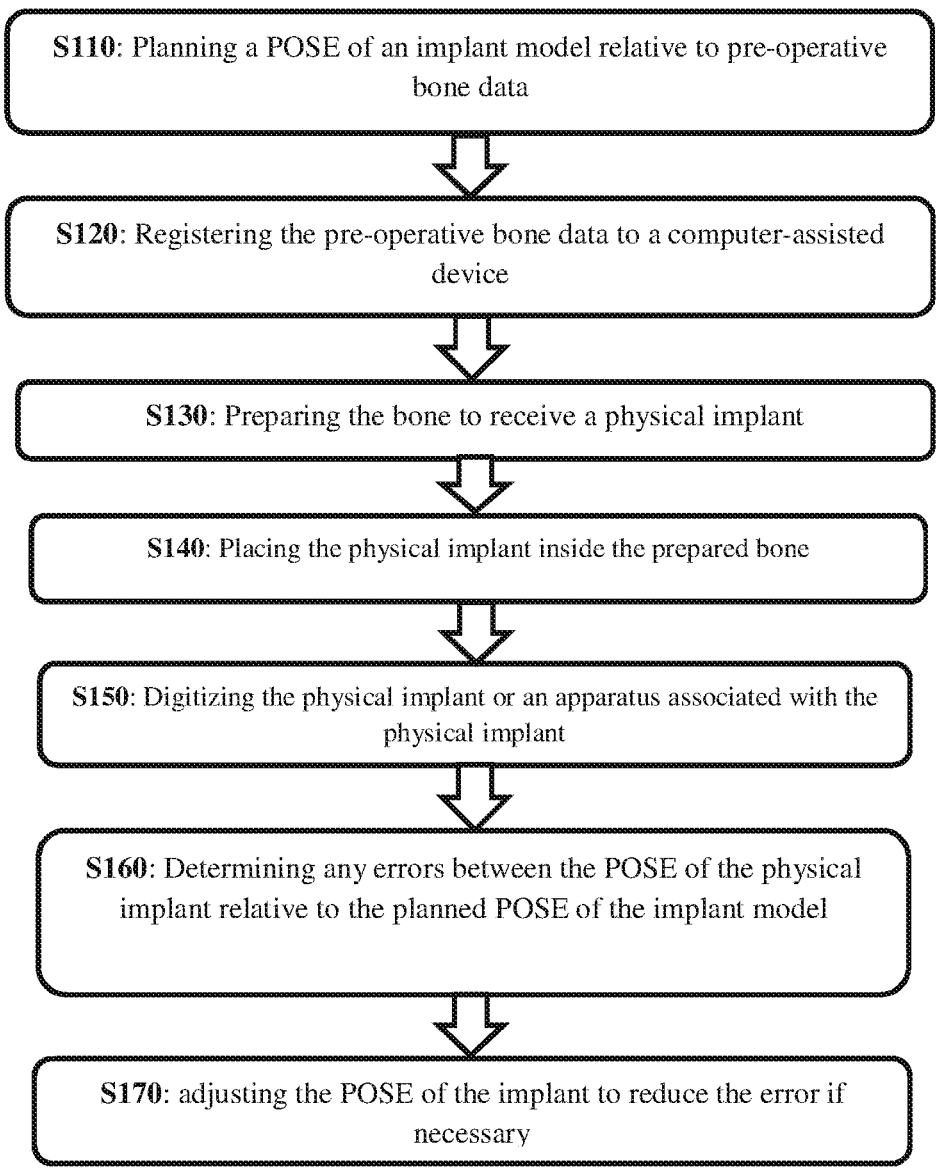
FIG. 1 is a flowchart depicting a method for verifying the placement of an implant with a connector apparatus in accordance with embodiments of the invention.

The present invention has utility as a system and method for measuring or verifying the placement of an implant within a bone in joint arthroplasty procedures. The system and method is especially advantageous for measuring and/or verifying the placement of the physical implant within the bone and comparing that placement with a pre-operatively planned placement during the procedure, intra-operatively. It should be appreciated that any computer-assisted surgical system including an autonomous, semi-autonomous, or passive robotic system either for medical or industrial applications can benefit from the device and methods disclosed herein.

The present invention will now be described with reference to the following embodiments. As is apparent by these descriptions, this invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment may be deleted from that embodiment. In addition, numerous variations and additions to the embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference in their entirety.

Definitions

Unless indicated otherwise, explicitly or by context, the following terms are used herein as set forth below.

As used in the description of the invention and the appended claims, the singular forms "a," "an" and "the" are intended to include the plural forms as well, unless the context clearly indicates otherwise.

Also, as used herein, "and/or" refers to and encompasses any and all possible combinations of one or more of the associated listed items, as well as the lack of combinations when interpreted in the alternative ("or").

As used herein, the term "digitizer" refers to a measuring device capable of measuring physical coordinates in three-dimensional space. For example, the 'digitizer' may be: a "mechanical digitizer" having passive links and joints, such as the high-resolution electro-mechanical sensor arm described in U.S. Pat. No. 6,033,415; a non-mechanically tracked digitizer probe (e.g., optically tracked, electromagnetically tracked, acoustically tracked, and equivalents thereof) as described for example in U.S. Pat. No. 7,043,961; or an end-effector of a robotic device.

As used herein, the term "digitizing" refers to the collecting, measuring, and/or recording of physical points in space with a digitizer.

As used herein, the term "pre-operative bone data" refers to bone data used to pre-operatively plan a procedure before making modifications to the actual bone. The pre-operative bone data may include one or more of the following. A patients actual exposed bone prior to modification, an image data set of a bone, a virtual generic bone model, a physical bone model, a virtual patient-specific bone model, or a set of data collected directly on a bone intra-operatively commonly used with imageless computer-assist devices.

As used herein, the term "registration" refers to the determination of the POSE and/or coordinate transformation between two or more objects or coordinate systems such as a computer-assist device, a bone, pre-operative bone data, surgical planning data (i.e., an implant model, cut-file, virtual boundaries, virtual planes, cutting parameters associated with or defined relative to the pre-operative bone data), and any external landmarks (e.g., a fiducial marker array) associated with the bone, if such landmarks exist. Methods of registration known in the art are described in U.S. Pat. Nos. 6,033,415, 8,010,177, and 8,287,522.

While the present invention is illustrated visually hereafter with respect to a femur as an example of the target bone for which the present invention is applied, it is appreciated that the present invention is equally applicable to other bones of a human, non-human primate, or other mammals.

Furthermore, it should be appreciated that while the systems and methods described herein teach the measuring and/or verification of the implant placement in hip arthroplasty, any of a wide variety of different bone implants may likewise be verified according to the teaching of this invention (e.g., a knee implant and shoulder implant).

Embodiments of the present invention describe a method and system for measuring and/or verifying the placement of an implant intra-operatively relative to a pre-operatively planned implant placement. The measurements may provide a user or a computer-assist device with information or recommendations on how to adjust the placement of the implant or modify the bone, if necessary, to reduce any error between the physical implant placements relative to the planned implant placement. It is further contemplated that the implant POSE measurements may be used for other applications other than implant adjustment or bone modification, including data collection for clinical publications and determining the accuracy of a particular tool in preparing a bone.

Referring now to the figures, FIG. 1 is an embodiment of a method for measuring and/or verifying the placement of an implant that generally includes the steps of (a) planning a position and orientation (POSE) of an implant model relative to pre-operative bone data (S110) (b) registering a bone and the pre-operative bone data to a computer-assist device (S120) (c) preparing the bone to receive a physical implant (S130) (d) placing the physical implant inside/on the bone (S140) (e) digitizing a plurality of points on the physical implant and/or an apparatus associated with the physical implant (S150) (f) determining any errors between at least a portion of the POSE of the physical implant relative to the planned POSE of the implant model using the plurality of digitized points (S160) and (g) adjusting, if necessary, the POSE of the physical implant to minimize any determined errors (S160). The adjusting step may further include guidance instructions provided by the system to guide the user on how to adjust the implant POSE to minimize any determined errors and better match the pre-operatively planned POSE. In one embodiment, the user with the aid of the guidance instructions performs the adjusting step, while in other embodiments the system automatically adjusts the implant POSE, or further modifies the bone, to minimize any determined errors. Various embodiments of the method and components are further described in detail below.

Generally, the user plans the POSE of an implant model relative to pre-operative bone data in a pre-operative planning software program having a graphical user interface (GUI). In a particular inventive embodiment, the pre-operative bone data is a virtual three-dimensional (3-D) bone model generated from an image data set of a subject's anatomy. The image data set may be collected with an imaging modality such as computed tomography (CT), dual-energy x-ray absorptiometry (DEXA), magnetic resonance imaging (MRI), X-ray scans, ultrasound, or a combination thereof. The 3-D bone model(s) are readily generated from the image data set using medical imaging software such as Mimics® (Materialise, Plymouth, MI) or other techniques known in the art such as the one described in U.S. Pat. No. 5,951,475. A set of 3-D computer aided design (CAD) models of the manufacturer's implants (implant models) are pre-loaded in the software that allows the user to place the components of a desired implant to the 3-D bone model of the boney anatomy to designate the best fit, position and orientation of the implant to the bone. The user can then save this surgical planning data to an electronic medium that is loaded and read by a computer-assisted device to assist the surgeon intra-operatively to prepare the bone to receive the physical implant.

Intra-operatively, at least one of the bone, the pre-operative bone data, surgical planning data, and any landmarks associated with the bone are registered to the computer-assist device (S120). For an imageless computer-assist device, the user may collect several points on a tracked bone to create a point cloud representation of the bone. During the point collection, the bone is inherently registered to the computer-assist device. Therefore, the user may plan the placement of the implant models relative to the point cloud representation of the bone after the bone is registered. Once the final planned implant placement is confirmed relative to the point cloud representation, the implant models are inherently registered to the computer-assist device. For image-guided computer-assist devices, registration may be performed with techniques known in the art (e.g., point-to-point, point-to-surface).

Subsequently, the bone is prepared (S130) (i.e., cut, shaved, or otherwise modified) to receive an implant according to the surgical plan. The bone may be prepared using a variety of different tools, either with manually tracked tools or other computer-assist devices. Examples of computer-assisted devices include: a tracking system (e.g., an optical tracking system, mechanical tracking system) for tracking one or more tools or a simple probe; a 1-6 degree of freedom or more hand-held surgical system; an autonomous serial-chain manipulator system; a haptic serial-chain manipulator system; a parallel robotic system; a robot mounted to the bone of the subject; a robotically maneuvered cut-guide; a tracked or navigated saw, broach, reamer, implant, or cut-guide; a master-slave robotic system; or any combination thereof. Such systems are described in U.S. Pat. Nos. 5,086,401, 6,757,582, 7,206,626, 8,571,638, 8,876,830, 8,961,536, and 9,283,048, U.S. Pat. App. Nos. 2008/0009697, 2013/0060278, and PCT Intl. App. No. US2015/051713. In a specific embodiment, the robotic system is as described below with reference to FIG. 10.

Once the bone is prepared, the surgeon places a physical implant in the prepared bone (S140). The surgeon may first use a trial implant to preliminarily assess how the final implant will affect the patient's range of motion, ligament balancing, and overall fit within the bone. After trialing, the surgeon inserts the final implant in the bone. As used herein, 'physical implant' may refer to either a trial implant and/or a final implant.

With the physical implant inserted in the prepared bone, at least a portion of the POSE of the implant is measured relative to the planned POSE of the implant model. The measurement begins by either digitizing a plurality of points on an apparatus assembled to the implant or by digitizing features manufactured directly on the physical implant (S150). A computer, controller, or processor associated with the computer-assist device may then determine any errors between the POSE of the physical implant relative to the planned POSE of the implant model based in part on the plurality of digitized points (S160). Embodiments of apparatuses, digitizable features manufactured on the implant, and the determination of the POSE of the physical implant relative to the POSE of the planned implant model is further described below.

In a particular inventive embodiment, with reference to FIGS. 2A-2C, an apparatus 300 to facilitate the measurement and/or verification of a femoral stem hip implant 100 is shown, where FIG. 2A is a perspective view of the apparatus 300 assembled to the implant 100, FIG. 2B is a top perspective view of the apparatus 300, and FIG. 2C is bottom perspective view of the apparatus 300. The apparatus 300 is configured to be positioned on a neck 110 of the implant 100 and includes features to facilitate the collection of a plurality of points with a digitizer. In more detail and as best shown in FIG. 2B-2C, the apparatus 300 is in the form of a cap having a body 310, a digitizing surface 320, and a receiving portion 330 for receiving the neck 110 therewithin. The digitizing surface 320 includes digitizing features to be digitized during the digitizing step. In a particular embodiment, the digitizing feature is a circular groove 340 engraved on the digitizing surface. In another embodiment, the digitizing feature is a circular ring of material projecting just above the digitizing surface 320.

In a specific inventive embodiment, the receiving portion 330 is an opening in the body 310, where the opening press-fits onto the neck 110. In another embodiment, the receiving portion 330 includes a snapping or screwing mechanism, which allows the apparatus 300 to removably couple to the implant 100 through a snapping or screwing mechanism. It should be appreciated that the receiving portion 330 may be in any form, shape, and size to fit on the neck 110 of the implant 100.

Figure 3A:
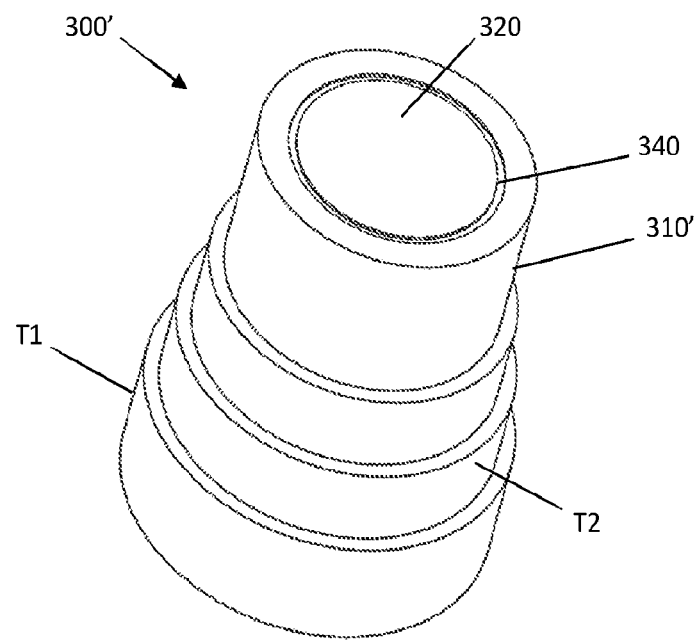
FIGS. 3A-3B depict a multi-size apparatus in accordance with embodiments of the invention, where
Figure 3B:
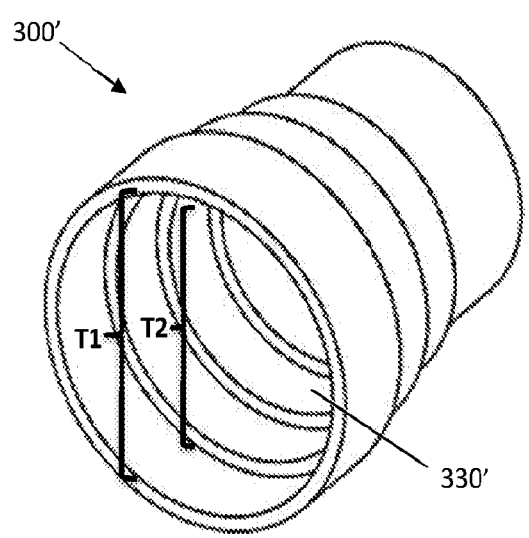

In another embodiment, with reference to FIGS. 3A-3B, an apparatus 300' to accommodate the measuring/verifying of implants 100 of various sizes is shown, where FIG. 3A is a top perspective view of the apparatus 300', and FIG. 3B is bottom perspective view thereof. The apparatus 300' includes a body 310' having several tiers (T1, T2, . . . , TN) of different inner diameters, each tier adapted to accommodate different sized implants. For example, with reference to FIG. 3B, an implant neck with a bigger size may fit within a larger inner diameter tier T1 and an implant neck with a smaller size may fit within a smaller inner diameter tier T2. Having an apparatus 300' with several tiers (T1, T2) is particularly advantageous. The different tiers allow the user to match differently size implant necks 110 without a need to change the apparatus 300' if the surgeon needs to change the size of the neck 110 intra-operatively. Second, the apparatus 300' may be sterilized and re-used for multiple surgeries, where different patients will require different sized implants.

The apparatus (300, 300') may be made of a rigid or semi-rigid material such as metal or plastic. Preferably, the apparatus (300, 300') is made of a biocompatible, sterilizable, semi-rigid plastic (e.g., silicone rubber) to easily press-fit over the neck 110 of the implant 100 but is not too flexible to affect point collection with the digitizer. However, it is contemplated that the apparatus (300, 300') may be made from a number of other materials with similar characteristics applicable for the purpose of this invention.

Figure 4:
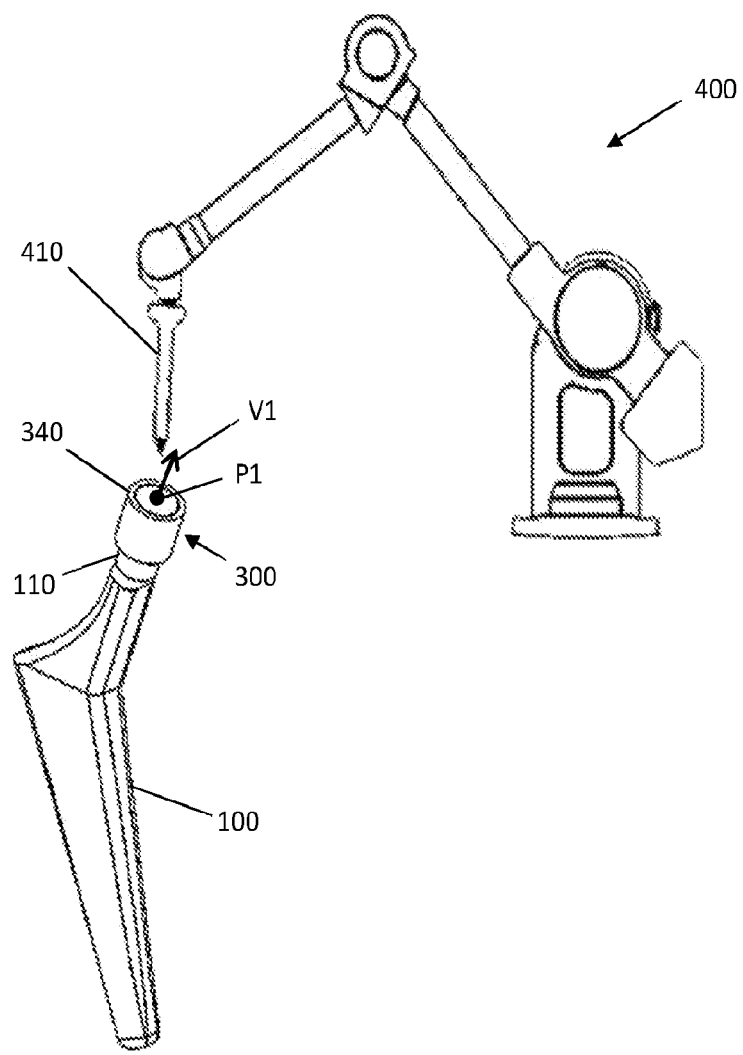
FIG. 4 depicts a perspective view of a digitizer registering a plurality of points on the apparatus while coupled to the implant in accordance with an embodiment of the invention.

The determination of the POSE of the physical implant with the apparatus (300, 300') and a digitizer begins by assembling the apparatus (300, 300') on the neck 110 of the implant 100 inserted in the bone. In a specific embodiment and referring to FIG. 4, the digitizer is a mechanical digitizer 400 having a probe 410. The user wields the probe 410 to digitize a plurality of points in the circular groove 340 engraved on the digitizing surface 320. A processor, controller, or computer associated with the digitizer or computer-assist device then calculates a median point P1 from the plurality of digitized points. The median point P1 represents the center of the circular groove 340 and therefor a point along the center axis of the neck 110. Following the calculation of the median point P1, two non-linear points may be chosen from the plurality of points collected on the groove 340 to calculate a vector normal V1 to the digitizing surface 320. The vector normal V1 represents the anteversion and inclination angles of the stem implant 100 in the bone, which may be compared to the planned anteversion and inclination angles as further described below.

Figures 5A, 5B:
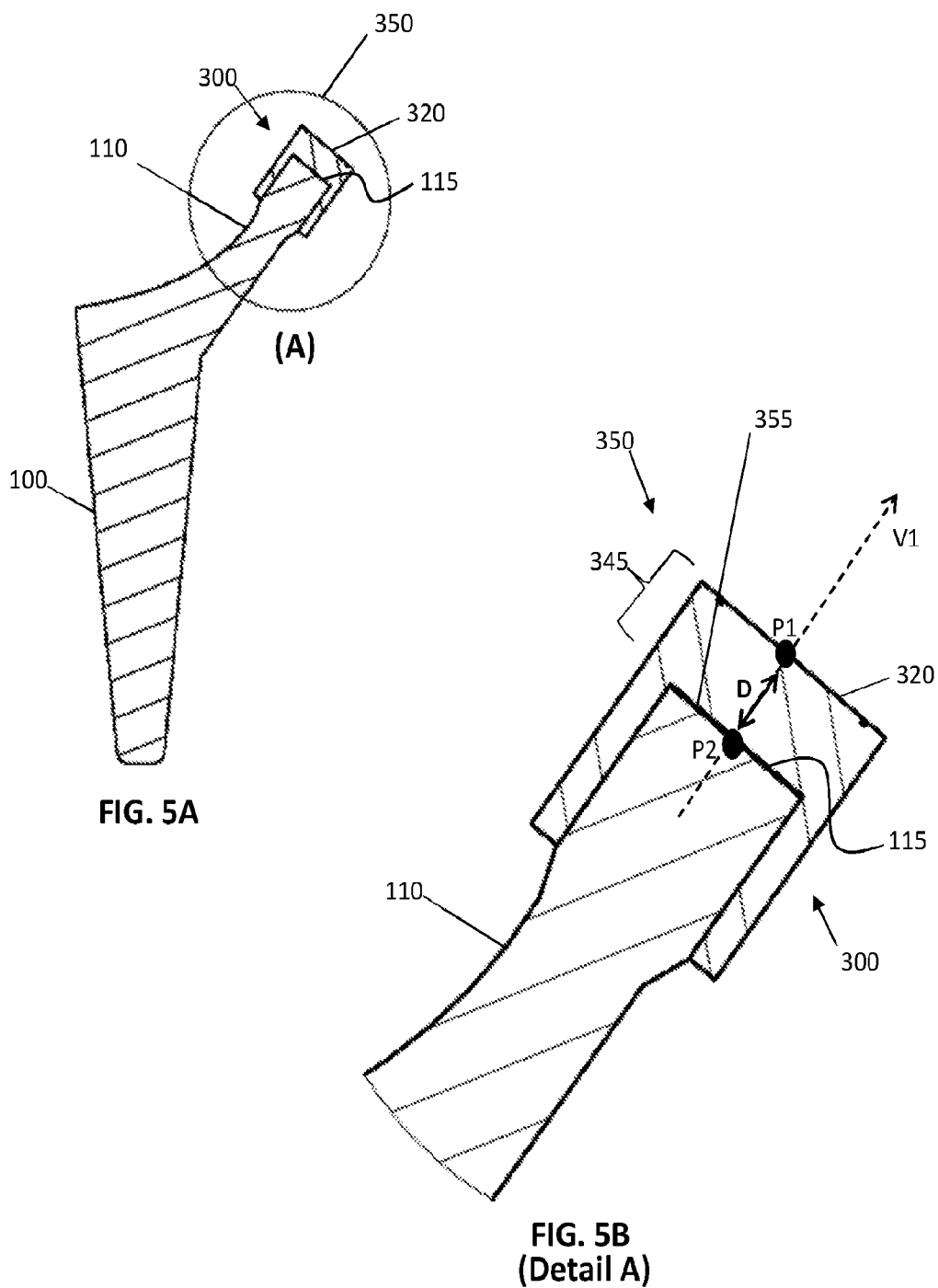
FIGS. 5A and 5B depict a cross-sectional view of the implant with the apparatus attached to the neck of the implant in accordance with an embodiment of the invention.

In another embodiment, with reference to FIGS. 5A-5B, a center neck point P2 located at the center of a top surface 115 of the neck 110 may be determined to define the translational position (leg length, offset, anterior-posterior position) of the implant. FIG. 5A depicts a longitudinal cross-sectional view of the apparatus 300 assembled to the implant 100 and FIG. 5B depicts a detailed view of the circled region 350 of FIG. 5A. After the median point P1 and normal vector V1 is calculated as described above, the center neck point P2 is determined by translating the median point P1 along the normal vector V1 by a known thickness D of a head portion 345 of the apparatus 300. The thickness of the head portion 345 is known per the manufacturing specifications and is defined as the distance between the digitizing surface 320, and an abutment surface 355 on the interior of the receiving portion 330 where the top surface 115 of the neck 110 abuts against when the apparatus 300 is assembled to the neck 110. Center neck point P2 defines the translational position of the implant 100 in the bone, such that the leg length, offset, and anterior-posterior position of the physical implant may also be compared to the planned leg length, offset, and anterior-posterior position.

Figure 6:
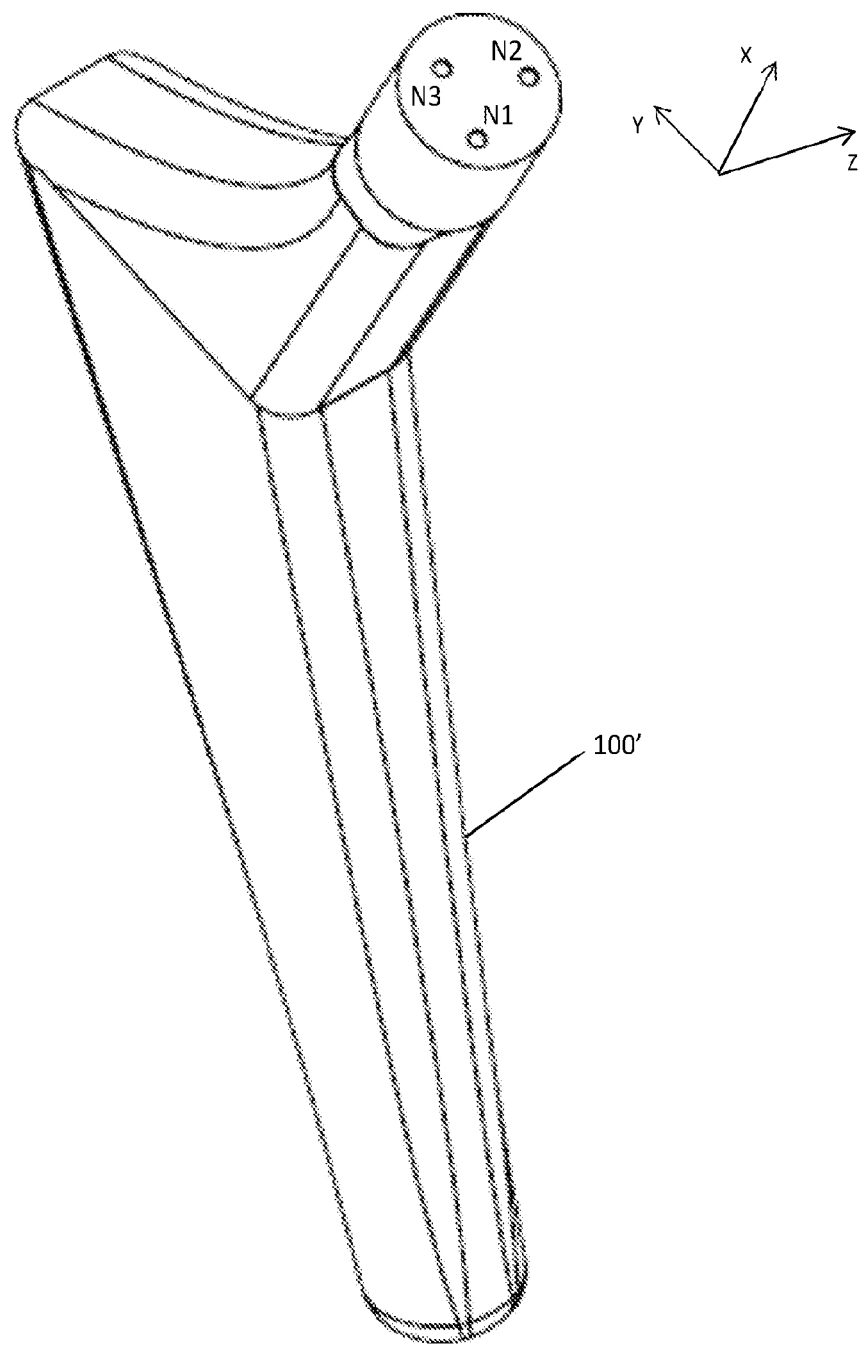
FIG. 6 depicts a perspective view of an implant with three known verification points located on a head of the implant in accordance with an embodiment of the invention.

In a specific inventive embodiment and referring to FIG. 6, another method for facilitating the collection of points to determine any POSE differences is shown. The physical implant 100' now includes three distinct points (N1, N2, N3) manufactured directly on a surface of the implant 100' in a known geometry and location. The corresponding implant model of the physical implant 100' also includes the three distinct points (N1, N2, N3) with the same geometry and at the same location such that a unique and shared coordinate system may be determined between the implant model and the physical implant. A method for determining the coordinate system and therefore the POSE of implant in the bone intra-operatively is as follows. After either a trial implant or a final implant is inserted in the bone, the user digitizes each point (N1, N2, N3). The order in which the points are digitized or designated may not be important, as long as the three points (N1, N2, N3) are not positioned in an equilateral or isosceles triangle. The system may identify each point (N1, N2, N3) based on the calculated lengths of each vector formed between the points (N1, N2, N3) such that the calculated orientation of the coordinate system of the physical implant may match with the orientation of the coordinate system of the corresponding implant model. If the order in which the points are digitized is important, the implant manufacturer may manufacture a small label of each point (N1, N2, N3) on the implant to designate which points (N1, N2, N3) are which. The coordinate system is calculated using traditional methods. For example, if the manufacturer designates N1 as the origin point, an X-axis may first be defined between points N1 and N2 as follows:

$$X \text{ axis} = \frac{N2 - N1}{\|N2 - N1\|}$$

A vector V2 can then be defined between points N1 and N3, as $$V2 = \frac{N3 - N1}{\|N3 - N1\|}$$

The Z axis is then defined as the unit vector of the cross product of the X axis and V2 and the Y axis is defined as the cross product of the X and Z axes.

Figures 7A, 7B:
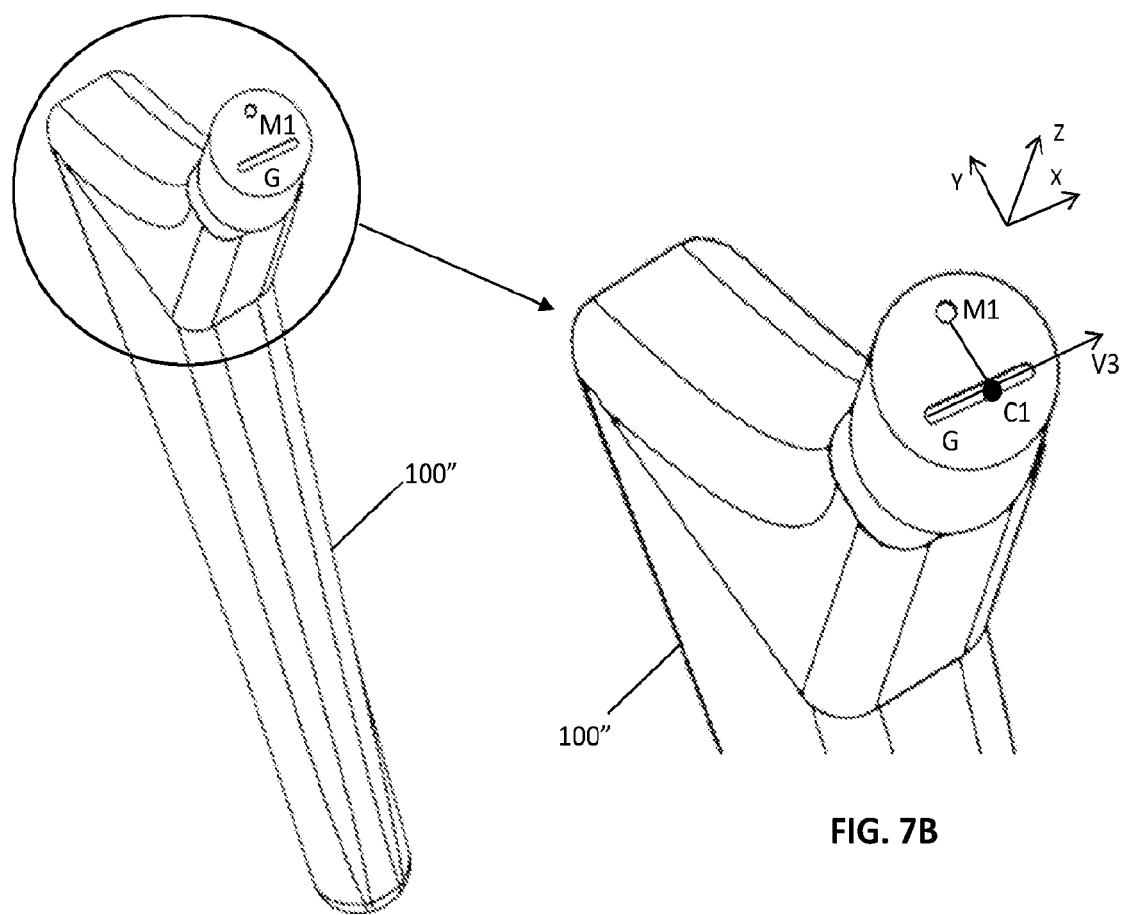
FIGS. 7A and 7B depict a perspective view of an implant with a verification point and a line located on the head of the implant in accordance with an embodiment of the invention.

In a particular inventive embodiment, with respect to FIGS. 7A and 7B, the implant 100" includes a distinct point M1 and a groove G manufactured directly on a surface of the implant 100" in a known geometry and location rather than three points (N1, N2, N3). The coordinate system may then be determined using the point M1 and groove G as follows:

a. A user with a digitizer collects the fixed point M1 on the implant.

b. The user with the digitizer collects several points (e.g., 10 or more) along the groove G, where the processor fits a line to the points to determine a vector V3. Note, here the user may collect the points on the groove prior to collecting the fixed point M1.

c. The processor then calculates a point C1 on the vector V3 that is the closest to point M1 (i.e., the perpendicular distance from point M1 to the vector V3. Point C1 is on a line through M1 that is perpendicular to the vector V3.

d. The processor can then determine a full coordinate system of the physical implant 100 with the vector V and points (M1, C1) using similar cross-product calculations as described for the three points (N1, N2, N3).

It should be appreciated that although the manufactured features (e.g., points (N1, N2, N3, M1) and groove G) are shown manufactured on a top surface of the neck of the implant (100', 100") in FIGS. 6-7B, the manufactured features may be manufactured on any surface of the implant as long as that surface is exposed and digitizable when the implant is implanted in the bone. Further, these manufactured features may be manufactured on any type of implant. Having these features on the implant is an invaluable tool to quickly and reliably determine the POSE of the implant in the bone compared to the pre-operatively planned placement.

Figure 8:
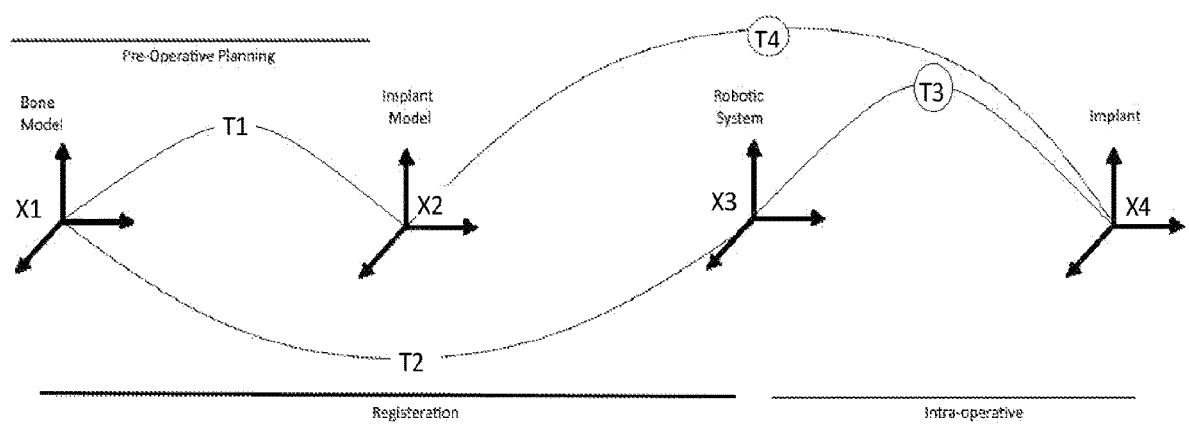
FIG. 8 depicts a pictorial representation illustrating coordinate systems and transformations according to embodiments of the present invention.

In order to determine any errors between the POSE of the physical implant relative to the planned POSE of the implant model (S160) several coordinate transformation need to be determined and/or calculated. FIG. 8 depicts several different coordinate systems associated with the systems and methods described herein including a first coordinate system X1 associated with the pre-operative bone data such as a virtual bone model, a second coordinate system X2 associated with the implant model, a third coordinate system X3 associated with the computer-assist device, and a fourth coordinate system X4 associated with the a physical implant. The fourth coordinate system X4 is either partially calculated (anteversion and inclination) using the apparatus (300, 300') and method described above, or fully calculated using the points (N1, N2, N3, M1) and/or groove G manufactured directly on the surface of the implant 100" as described above in FIGS. 7A and 7B.

A first coordinate transformation T1 is a transformation from the coordinate system of the pre-operative bone data X1 to the coordinate system of the implant model X2 in the pre-operative planning stage. T1 is calculated and fixed after the user plans the POSE of the implant model relative to the pre-operative bone data. A second coordinate transformation T2 is a transformation from the coordinate system computer-assist device X3 to the coordinate system of the pre-operative bone data X1. The second coordinate transformation T2 is determined by registering the physical anatomy of the patient and the pre-operative bone data to the computer-assist device. The third coordinate transformation T3 is a transformation from the coordinate system of the computer-assist device X3 to the coordinate system of the physical implant X4. The third coordinate transformation T3 is determined while digitizing the apparatus (300, 300') or digitizing the points (N1, N2, N3, M1) and/or groove G directly on the implant. Lastly, the fourth transformation T4 between the planned implant model coordinate system X2 and the actual implant coordinate system X4 positioned in the bone is calculated as described below:

$$^{X2}T_{1\times1}\cdot{}^{X1}T_{2\times3}={}^{X2}T_{X3} \qquad a.$$

$$^{X4}T_{3\times3}\cdot({}^{X2}T_{X3})^{-1}={}^{X4}T_{4\times2}$$

Figure 9:
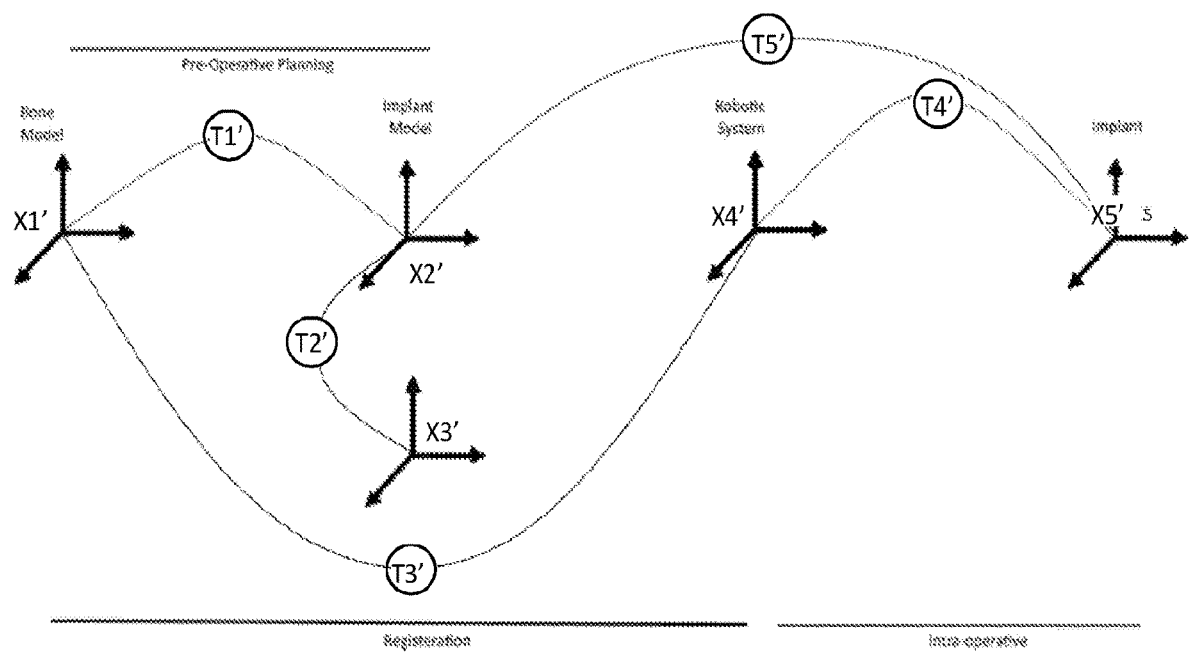
FIG. 9 depicts a pictorial representation illustrating coordinate systems and transformations according to embodiments of the present invention.

In a specific inventive embodiment, an additional coordinate system may be associated with the implant model other than the base coordinate system defined in the CAD software. The additional coordinate systems may include the coordinate system defined by the three points (N1, N2, N3), or a second coordinate system defined by a third-party that generates cut-files having cutting parameters or cut-paths associated with the geometry of the implant, where this second coordinate system provides a better baseline for defining specific cut-paths or cutting path geometries with respect to the implant model. FIG. 9 depicts several different coordinate systems for this scenario including a first coordinate system X1' associated with the pre-operative bone data illustratively including a virtual bone model, a second coordinate system X2' associated with the implant model (e.g., a base coordinate system from the CAD file), an additional third coordinate system X3' (e.g., associated with the three manufactured points (N1, N2, N3)), a fourth coordinate system X4' associated with the computer-assist device, and a fifth coordinate system X5' associated with the physical implant.

Continuing with FIG. 9, a first coordinate transformation T1' is a transformation from the coordinate system of the pre-operative bone data X1' to the coordinate system of the implant model X2' in the pre-operative planning stage. A second coordinate transformation T2' is a transformation from the additional coordinate system associated with the implant model X3' to a base coordinate system of the implant model X2'. The third coordinate transformation T3' is a transformation from the coordinate system computer-assist device X4' to the coordinate system of the pre-operative bone data X1'. The third coordinate transformation T3' is determined by registering the physical anatomy of the patient and the pre-operative bone data to the computer-assist device. The fourth coordinate transformation T4' is a transformation from the coordinate system of the computer-assist device X4' to the coordinate system of the physical implant X5'. The fourth coordinate transformation T4' is determined with the digitizing the apparatus (300, 300') or digitizing the points (N1, N2, N3, M1) and/or groove G directly on the implant. Lastly, the fifth transformation T5' between the manufactured three points X3' and the physical implant X5' is calculated by:

$$^{X1'}T_{X2'}\cdot{}^{X2'}T_{X3'}={}^{X1'}T_{X3'} \qquad a.$$

$$({}^{X1'}T_{X4'})^{-1}\cdot{}^{X1'}T_{X3'}={}^{X4'}T_{X3'} \qquad b.$$

$$({}^{X4'}T_{X5'})^{-1}\cdot{}^{X4'}T_{X3'}={}^{X5'}T_{X3'} \qquad c.$$

T4 in FIG. 8 and T5' in FIG. 9 provide any error between the POSE of the physical implant and the POSE of the planned implant. Any determined errors provide the surgeon with valuable information that may be acted upon in various ways. In one scenario, the user and/or computer-assist device may adjust the POSE of one or more physical implants to minimize the errors (S170). The adjustment may be performed in several ways illustratively including: physically detaching the implant from the bone and adjusting the implant to a more accurate position; slightly adjusting the POSE of the implant while inside the bone; making additional modifications to the bone; changing the size of one or more modular components (e.g., the size of a femoral head or neck); or adjusting the POSE of a second implant to obtain an overall alignment goal (e.g., adjusting the anteversion of an acetabular cup 130, without adjusting the femoral stem 100, to obtain a desired combined anteversion). The determined errors may also be used for data collection to assess the efficacy of the device or for the collection of publication data.

Robotic System

Figure 10:
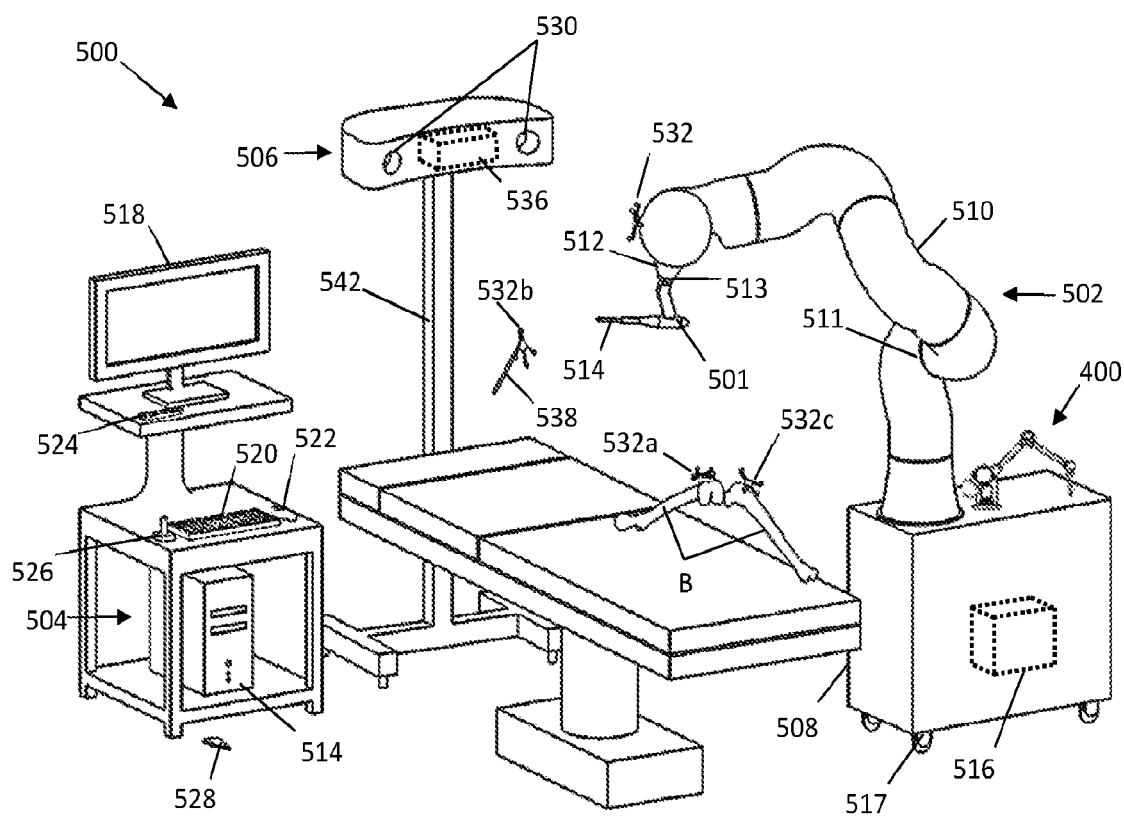
FIG. 10 illustrates a surgical system in the context of an operating room (OR) for executing a revision procedure in accordance with embodiments of the invention.

With reference to FIG. 10, an embodiment of a robotic surgical system is shown generally at 500 capable of implementing embodiments of the inventive method described above. The surgical system 500 generally includes a surgical robot 502, a computing system 504, and may include at least one of a mechanical digitizer arm 400 or an optical tracking system 506.

The surgical robot 502 may include a movable base 508, a manipulator arm 510 connected to the base 508, an end-effector flange 512 located at a distal end of the manipulator arm 510, and an end-effector assembly 501 for holding and/or operating a tool 514 removably attached to the flange 512 by way of an end-effector mount 513. The base 508 may include an actuator 511 to adjust the height of the robotic arm 510. The base may further include a set of wheels 517 to maneuver the base 508, which may be fixed into position using a braking mechanism such as a hydraulic brake. The manipulator arm 510 includes various joints and links to manipulate the tool 514 in various degrees of freedom. If a mechanical digitizer 400 or optical tracking system 506 is not present, the tool 514 may be fitted with a probe tip to collect points on the recovery markers directly. The joints are illustratively prismatic, revolute, or a combination thereof.

The computing system 504 generally includes a planning computer 514; a device computer 516; a tracking computer 536 if a tracking system 506 is present; and peripheral devices. The planning computer 514, device computer 516, and tracking computer 536, may be separate entities, single units, or combinations thereof depending on the surgical system. The peripheral devices allow a user to interface with the surgical system components and may include: one or more user-interfaces, such as a display or monitor 518 for the graphical user interface (GUI); and user-input mechanisms, such as a keyboard 520, mouse 522, pendent 524, joystick 526, foot pedal 528, or the monitor 518 in some inventive embodiments have touchscreen capabilities.

The planning computer 514 contains hardware (e.g., processors, controllers, and/or memory), software, data and utilities that are in some inventive embodiments dedicated to the planning of a surgical procedure, either pre-operatively or intra-operatively. This may include reading medical imaging data, segmenting imaging data, constructing three-dimensional (3D) virtual models, storing computer-aided design (CAD) files, providing various functions or widgets to aid a user in planning the surgical procedure, and generating surgical plan data. The final surgical plan may include image data, patient data, registration data, implant position data, and/or operational data. The operational data may be a set of instructions for modifying a volume of tissue that is defined relative to the anatomy, such as a set of cutting parameters (e.g., cut paths, velocities) in a cut-file to autonomously modify the volume of bone, a set of virtual boundaries defined to haptically constrain a tool within the defined boundaries to modify the bone, a set of planes or drill holes to drill pins in the bone, or a graphically navigated set of instructions for modifying the tissue. In particular inventive embodiments, the operational data specifically includes a cut-file for execution by a surgical robot to autonomously modify the volume of bone, which is advantageous from an accuracy and usability perspective. The final surgical plan data further includes the planned POSE data for the implant including any coordinate system and transformation data to measure the POSE differences as described above. The surgical plan data generated from the planning computer 514 may be transferred to the device computer 516 and/or tracking computer 536 through a wired or wireless connection in the operating room (OR); or transferred via a non-transient data storage medium (e.g., a compact disc (CD), a portable universal serial bus (USB) drive) if the planning computer 514 is located outside the OR.

The device computer 516 in some inventive embodiments is housed in the moveable base 508 and contains hardware, software, data and utilities that are preferably dedicated to the operation of the surgical device 502. This may include surgical device control, robotic manipulator control, the processing of kinematic and inverse kinematic data, the execution of registration algorithms, the execution of calibration routines, the execution of operational data (e.g., cut-files), coordinate transformation processing, providing workflow instructions to a user, and utilizing position and orientation (POSE) data from the tracking system 506. The device computer 516 further computes and measures the errors between the planned POSE of the implant and the actual POSE of the implant using the techniques described herein.

The optional tracking system 506 of the surgical system 500 includes two or more optical receivers 530 to detect the position of fiducial markers (e.g., retroreflective spheres, active light emitting diodes (LEDs)) uniquely arranged on rigid bodies. The fiducial markers arranged on a rigid body are collectively referred to as a fiducial marker array 532, where each fiducial marker array 532 has a unique arrangement of fiducial markers, or a unique transmitting wavelength/frequency if the markers are active LEDs. An example of an optical tracking system is described in U.S. Pat. No. 6,061,644. The tracking system 506 may be built into a surgical light, located on a boom, a stand 542, or built into the walls or ceilings of the OR. The tracking system computer 536 may include tracking hardware, software, data and utilities to determine the POSE of objects (e.g., bones B, surgical device 502) in a local or global coordinate frame. The POSE of the objects is collectively referred to herein as POSE data, where this POSE data may be communicated to the device computer 516 through a wired or wireless connection. Alternatively, the device computer 516 may determine the POSE data using the position of the fiducial markers detected from the optical receivers 530 directly.

The POSE data is determined using the position data detected from the optical receivers 530 and operations/processes such as image processing, image filtering, triangulation algorithms, geometric relationship processing, registration algorithms, calibration algorithms, and coordinate transformation processing. For example, the POSE of a digitizer probe 538 with an attached probe fiducial marker array 532b may be calibrated such that the probe tip is continuously known as described in U.S. Pat. No. 7,043,961. The POSE of the tool tip or tool axis of the tool 514 may be known with respect to a device fiducial marker array 532 using a calibration method as described in U.S. Prov. Pat. App. 62/128,857. It should be appreciated that even though the device fiducial marker 532 is depicted on the manipulator arm 510, it may also be positioned on the base 508 or the end-effector assembly 501. Registration algorithms may be executed to determine the POSE and coordinate transforms between a bone B, pre-operative bone data, a fiducial marker array 532a or 532c, and a surgical plan, using the registration methods described in U.S. Pat. Nos. 6,033,415, and 8,287,522.

Upon assembly of the device tracking array 532 to the surgical robot 502 prior to surgery, the POSE's of the coordinate systems, 532 and the end effector tool 514, are fixed relative to each other and stored in memory to accurately track the end effector tool 514 during the surgery (see for example U.S. Patent Publication 20140039517 A1) relative to the bone anatomy (e.g., bones B). The POSE data may be used by the computing system 504 during the procedure to update the bone and surgical plan coordinate transforms so the surgical robot 502 can accurately execute the surgical plan in the event any bone motion occurs. It should be appreciated that in certain embodiments, other tracking systems may be incorporated with the surgical system 500 such as an electromagnetic field tracking system or a 6-DOF mechanical tracking system. An example of a 6-DOF mechanical tracking system is described in U.S. Pat. No. 6,322,567. In a particular inventive embodiment, the surgical system 500 does not include a tracking system 506, but instead employs a bone fixation and monitoring system that fixes the bone directly to the surgical robot 502 in the robotic coordinate frame and monitors bone movement as described in U.S. Pat. No. 5,086,401.

EXAMPLES

The following examples are demonstrative of the scope of the embodiments described herein. The examples are intended to illustrate how specific embodiments of the systems and methods described herein may be combined and executed, but are in no way meant to be limiting.

Example 1

In an implementation of an embodiment of the inventive method to measure and verify a femoral stem implant for THA relative to the planned femoral stem implant placement involves a three-step protocol which includes pre-operative planning, intra-operative registration, and intra-operative bone modification, measurement/verification, and adjustment, if necessary.

An embodiment of the pre-operative planning includes the steps of: acquiring a CT scan of a femur and pelvis of a patient; generating a 3D model of the bones based on the CT scan images; determining the implant make/model/size which best fit to the position and orientation of the bone. Saving the surgical planning data to an electronic medium that is loaded and read by a computer-assisted device such as an autonomous serial-chain manipulator system as described in U.S. Pat. No. 5,086,401 to assist the surgeon intra-operatively to prepare the bone to receive a physical implant.

In the next step, the bone and surgical planning data is registered to the computer-assist device. The registration steps include: using a mechanical digitizer 400 to collect a plurality of points on the bone and correlating the acquired points on the bone to the 3D model of the bone.

An inventive embodiment of the bone modification procedure includes: milling the proximal portion of the femoral bone with an end-mill operated by a robot manipulator arm; inserting a trial implant in the intramedullary canal of the femur; inserting an apparatus on the implant neck; registering a plurality of points on the groove of the apparatus as shown in FIGS. 2A-2C; and calculating the transformation between the trial implant relative to the planned implant three dimensional (3-D) model to determine any error between the POSE of the trial implant relative to the POSE of the implant model. Following the measurement step, if the level of error is not within an acceptable range, the user may exchange modular components of the trial, change the size of the trial, or re-modify the bone such that the final implant fits in the bone in a POSE more associated with planned implant POSE. For example, if the inclination angle of the trial implant is more than 5 degrees compared to the 3D model of the implant in the pre-operative planning, the user may remove the trial implant, re-mill the bone with the manipulator to adjust the cavity according to the error, re-asses the placement of a new trial implant, insert the final implant in the bone, and re-verify/measure the final implant placement.

Example 2

In an implementation of an embodiment of the inventive method to measure and verify knee implant components for TKA relative to the planned knee implant component placement involves a three-step protocol which includes pre-operative planning, intra-operative registration, and intra-operative bone modification, measurement/verification, and adjustment, if necessary.

An embodiment of the pre-operative planning includes the steps of: acquiring a CT scan of a femur and tibia of a patient; generating a 3D model of the bones based on the CT scan images; determining the implant make/model/size which best fit to the position and orientation of the bone to restore the mechanical axis of the patient's leg. Saving the surgical planning data to an electronic medium that is loaded and read by a computer-assisted device such as a 2-DOF hand-held device as described in Int'l. Pat. App. No. PCT/US16/62020 to assist the surgeon intra-operatively to prepare the bone to receive the physical implants.

In the next step, the bone and surgical plan are registered to the computer-assist device. The registration steps include: using an optical tracking system and an optically tracked digitizing probe to collect a plurality of points on the bone and correlating the acquired points on the bone to the 3D model of the bone.

An inventive embodiment of the intraoperative protocol includes: cutting the proximal portion of the tibia with the 2-DOF hand-held device according to the surgical plan; inserting a trial implant having three points (e.g., N1, N2, N3) manufactured on the implant on the bone; digitizing the three points on the implant; calculating the transformation between the trial implant relative to the implant's 3-D model to determine the error between the POSE of the trial implant relative to the POSE of the implant model. Following the measurement step, if the level of error is not within an acceptable range, the user may exchange modular components of the trial, change the size of the trial, or re-modify the bone such that the final implant fits in the bone in a POSE more associated with planned implant POSE.

Other Embodiments

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient roadmap for implementing the exemplary embodiment or exemplary embodiments. It should be understood that various changes can be made in the function and arrangements of elements without departing from the scope as set forth in the appended claims and the legal equivalents thereof.

The invention claimed is:

1. A method for comparing a position of an implant mounted to a bone with a planned position for the implant with respect to the bone, the method comprising:
   recording locations of a plurality of points as indicated by a digitizer probe when the digitizer probe is in contact with at least one digitizing feature of an apparatus that is coupled to the implant, and wherein the at least one digitizing feature is formed on a surface of the apparatus or projecting from the surface of the apparatus, the apparatus adapted to be selectively decoupled from the implant; and
   comparing a position and/or orientation (POSE) of the implant mounted to the bone with a planned POSE for the implant with respect to the bone using the plurality of points;

wherein the apparatus comprises a body having a series of tiers of different diameters, each tier adapted to accommodate different sized implants.

2. The method of claim 1 further comprising displaying results of the comparison.

3. The method of claim 1 further comprising adjusting the POSE of the implant to minimize errors between the POSE of the implant mounted to the bone and the planned POSE of the implant with respect to the bone by either: a) modifying the bone; b) adjusting a position of a component of the implant; c) modifying the implant; d) adding one or more additional implant components; or e) a combination thereof.

4. The method of claim 1 wherein the comparison determines errors between the POSE of the implant mounted to the bone and the planned POSE for the implant with respect to the bone.

5. The method of claim 1, wherein the planned POSE for the implant with respect to the bone corresponds to a planned POSE of an implant model with respect to pre-operative bone data.

6. The method of claim 5 wherein the pre-operative bone data is a virtual bone model.

7. The method of claim 1 wherein the apparatus further comprises a receiving portion configured to couple to at least a portion of the implant.

8. The method of claim 1 wherein the at least one digitizing feature is a groove engraved on the surface or material projecting above the surface.

9. A surgical system for performing the method of claim 1, the system comprising:
the digitizer probe; and
a computer comprising a processor configured to compare a position and/or orientation (POSE) of the implant mounted to the bone with a planned POSE for the implant with respect to the bone using the plurality of points.

10. A method for comparing a position of an implant mounted to a bone with a planned position for the implant with respect to the bone, the method comprising:
recording locations of a plurality of points as indicated by a digitizer probe when the digitizer probe is in contact with at least one digitizing feature of an apparatus that is coupled to the implant, and wherein the digitizing feature is formed on a surface of the apparatus or projecting from the surface of the apparatus, the apparatus adapted to be selectively decoupled from the implant;
comparing a position and/or orientation (POSE) of the implant mounted to the bone with a planned POSE for the implant with respect to the bone using the plurality of points; and
wherein a computer calculates a vector normal to the surface of the apparatus using the plurality of points, wherein the vector normal represents an orientation of the implant mounted to the bone.

11. The method of claim 10, wherein the planned POSE for the implant with respect to the bone corresponds to a planned POSE of an implant model with respect to pre-operative bone data.

12. The method of claim 11 wherein the pre-operative bone data is a virtual bone model.

13. The method of claim 10 wherein the apparatus further comprises a receiving portion configured to couple to at least a portion of the implant.

14. The method of claim 10 wherein the at least one digitizing feature is a groove engraved on the surface or material projecting above the surface.

15. The method of claim 10 further comprising displaying results of the comparison.

16. The method of claim 10 further comprising adjusting the POSE of the implant to minimize errors between the POSE of the implant mounted to the bone and the planned POSE of the implant with respect to the bone by either: a) modifying the bone; b) adjusting a position of a component of the implant; c) modifying the implant; d) adding one or more additional implant components; or e) a combination thereof.

17. The method of claim 10 wherein the comparison determines errors between the POSE of the implant mounted to the bone and the planned POSE for the implant with respect to the bone.

18. A surgical system for performing the method of claim 10, the system comprising:
the digitizer probe; and
a computer comprising a processor configured to compare a position and/or orientation (POSE) of the implant mounted to the bone with a planned POSE for the implant with respect to the bone using the plurality of points.

19. A method for determining errors between a position of an implant mounted to a bone and a planned position for the implant with respect to the bone, the method comprising:
digitizing a plurality of points located on an implant mounted to the bone, wherein the implant comprises at least one digitizing feature on a surface of the implant to facilitate the digitization of the plurality of points; and
determining errors, using the plurality of digitized points, between a position and/or orientation (POSE) of the implant mounted to the bone and a planned POSE for the implant with respect to the bone;
wherein the at least one digitizing feature comprises a point and a groove, wherein the location of the point and the groove are digitized to calculate a coordinate system of the implant mounted to the bone.

20. The method of claim 19, wherein the planned POSE for the implant with respect to the bone corresponds to a planned POSE of an implant model with respect to pre-operative bone data, wherein the pre-operative bone data is a virtual bone model generated from an image data set of the bone.

21. A method for comparing a position of an implant mounted to a bone with a planned position for the implant with respect to the bone, the method comprising:
recording locations of a plurality of points as indicated by a digitizer probe when the digitizer probe is in contact with at least one digitizing feature of an apparatus that is coupled to the implant, and wherein the at least one digitizing feature is formed on a surface of the apparatus or projecting from the surface of the apparatus, the apparatus adapted to be selectively decoupled from the implant; and
comparing a position and/or orientation (POSE) of the implant mounted to the bone with a planned POSE for the implant with respect to the bone using the plurality of points;
wherein the digitizer probe comprises a probe tip, wherein a location of the probe tip in contact with the at least one digitizing feature indicates a location of a point from the plurality of points.

22. The method of claim 21, wherein the planned POSE for the implant with respect to the bone corresponds to a planned POSE of an implant model with respect to pre-operative bone data.

23. The method of claim 22 wherein the pre-operative bone data is a virtual bone model.

24. The method of claim 21 wherein the apparatus further comprises a receiving portion configured to couple to at least a portion of the implant.

25. The method of claim 21 wherein the at least one digitizing feature is a groove engraved on the surface or material projecting above the surface.

26. The method of claim 21 further comprising displaying results of the comparison.

27. The method of claim 21 further comprising adjusting the POSE of the implant to minimize errors between the POSE of the implant mounted to the bone and the planned POSE of the implant with respect to the bone by either: a) modifying the bone; b) adjusting a position of a component of the implant; c) modifying the implant; d) adding one or more additional implant components; or e) a combination thereof.

28. The method of claim 21 wherein the comparison determines errors between the POSE of the implant mounted to the bone and the planned POSE for the implant with respect to the bone.

29. A surgical system for performing the method of claim 21 the system comprising:
   the digitizer probe; and
   a computer comprising a processor configured to compare a position and/or orientation (POSE) of the implant mounted to the bone with a planned POSE for the implant with respect to the bone using the plurality of points.

* * * * *